United States Patent
Shields et al.

(10) Patent No.: US 10,087,002 B2
(45) Date of Patent: Oct. 2, 2018

(54) SYSTEMS AND METHODS FOR DELIVERING MERCHANDISE ITEMS USING A CONVEYOR APPARATUS

(71) Applicant: Wal-Mart Stores, Inc., Bentonville, AR (US)

(72) Inventors: David C. Shields, Bentonville, AR (US); Daniel R. Shields, Cave Springs, AR (US)

(73) Assignee: WALMART APOLLO, LLC, Bentonville, AR (US)

( * ) Notice: Subject to any disclaimer, the term of this patent is extended or adjusted under 35 U.S.C. 154(b) by 0 days.

(21) Appl. No.: 15/468,335

(22) Filed: Mar. 24, 2017

(65) Prior Publication Data

US 2017/0291767 A1 Oct. 12, 2017

Related U.S. Application Data

(60) Provisional application No. 62/319,067, filed on Apr. 6, 2016.

(51) Int. Cl.
*B65G 1/137* (2006.01)
*G06K 7/14* (2006.01)
(Continued)

(52) U.S. Cl.
CPC .......... *B65G 1/1373* (2013.01); *B65G 1/1376* (2013.01); *B65G 43/00* (2013.01);
(Continued)

(58) Field of Classification Search
CPC ............................. B65G 1/1373; B65G 1/1376
See application file for complete search history.

(56) References Cited

U.S. PATENT DOCUMENTS 5,597,995 A 1/1997 Williams
6,464,142 B1 10/2002 Denenberg
(Continued)

OTHER PUBLICATIONS

Vertical Storage Systems; "KardexRemstar Products—Industry Focus—Pharmacy Automation"; http://verticalstoragesystems.com/kardexremstar/industry-focus/pharmacy-automation/; Jan. 27, 2016; 1.

(Continued)

*Primary Examiner* — Thomas Randazzo
(74) *Attorney, Agent, or Firm* — Fitch, Even, Tabin & Flannery LLP (57) ABSTRACT

In some embodiments, apparatuses and methods are provided herein useful to delivering merchandise items using a conveyor apparatus. Some of these embodiments include systems for delivering merchandise items comprising: a conveyor apparatus having unique conveyor locations for deposit of a merchandise item, the conveyor apparatus extending between a first controlled access point and a second, different controlled access point; a first input interface configured to enter identifying information regarding the merchandise item and to associate it with a corresponding unique conveyor location in the conveyor apparatus where the merchandise item is deposited; a second input interface configured to enter customer identification information; and a controller configured to receive information from the first input interface and the second input interface and to activate the conveyor apparatus to move the corresponding unique location of the merchandise item to the second controlled access point.

22 Claims, 6 Drawing Sheets

(51) Int. Cl.
    *G06K 19/06*     (2006.01)
    *G07G 1/14*     (2006.01)
    *G06F 19/00*     (2018.01)
    *G06Q 50/28*     (2012.01)
    *B65G 43/00*     (2006.01)
    *G06Q 10/08*     (2012.01)

(52) U.S. Cl.
    CPC ....... *G06F 19/3462* (2013.01); *G06K 7/1413* (2013.01); *G06K 19/06028* (2013.01); *G06Q 10/087* (2013.01); *G06Q 50/28* (2013.01); *G07G 1/14* (2013.01)

(56) References Cited

U.S. PATENT DOCUMENTS

| | | | |
|---|---|---|---|
| 6,847,861 B2 | 1/2005 | Lunak | |
| 6,883,681 B1 | 4/2005 | Coughlin | |
| 6,892,941 B2* | 5/2005 | Rosenblum | G06F 19/3462 235/375 |
| 7,111,780 B2 | 9/2006 | Broussard | |
| 7,194,333 B2 | 3/2007 | Shoenfeld | |
| 8,145,353 B1* | 3/2012 | Cotner | G07F 17/0092 700/236 |
| 8,306,651 B2 | 11/2012 | Chudy | |
| 8,494,672 B2* | 7/2013 | Chirnomas | B65G 1/1373 700/215 |
| 9,745,131 B2* | 8/2017 | Hawkes | B65G 1/1376 |
| 2005/0049746 A1* | 3/2005 | Rosenblum | G06F 19/3462 700/232 |
| 2006/0016824 A1 | 1/2006 | Guerra | |
| 2010/0172724 A1* | 7/2010 | Hawkes | B65G 1/0471 414/266 |
| 2011/0153064 A1* | 6/2011 | Fellows | B65G 1/045 700/218 |
| 2012/0118910 A1 | 5/2012 | Pinney | |
| 2012/0305638 A1 | 12/2012 | Szesko | |
| 2014/0025545 A1 | 1/2014 | Carson | |
| 2017/0301004 A1* | 10/2017 | Chirnomas | G06Q 30/0635 |

OTHER PUBLICATIONS

PCT; PCT/US2017/025901; International Search Report and Written Opinion dated Jun. 16, 2017.

* cited by examiner

SYSTEMS AND METHODS FOR DELIVERING MERCHANDISE ITEMS USING A CONVEYOR APPARATUS

RELATED APPLICATION

This application claims the benefit of U.S. Provisional Application No. 62/319,067, filed Apr. 6, 2016, which is incorporated herein by reference in its entirety.

TECHNICAL FIELD

This invention relates generally to delivering merchandise items using a conveyor apparatus and, in particular, to delivering merchandise items at a shopping facility.

BACKGROUND

In the retail setting, tasks for delivering merchandise items to a customer are frequently divided between several employees within a shopping facility. For example, when a customer places an order, one employee may be responsible for identifying and locating the merchandise item from a shopping facility merchandising area (or filling the order) and then placing the merchandise item in a common employee area (binning) for pick-up by a second employee. In turn, when the customer picks up the order, the second employee may be responsible for identifying the order, locating the merchandise item within the common area, transporting the merchandise item to a cashier area, and then completing the sales transaction.

In some retail settings, this inefficient staging of merchandising items can cause some delays for customer pick-up and some frustration for both shopping facility employees and customers. Some merchandising systems require a manual binning and picking system to manage the staging of merchandise for customer pick-up. When an order filler is done identifying and gathering the merchandise item, the item may be placed into a container or bin along with other merchandise items for other customers. One container may contain numerous merchandise items for various customers. There may be some sort of system that records the container location (as there may be many such containers in the common employee area), or the binning may be handled according to an alphabetical approach or based on space availability within the containers. When the customer arrives for pick-up, the sales associate or cashier may then look up the container location for that customer's merchandise item, identify and locate the correct container, and then search within the container for the merchandise item for the applicable customer inside the container. The manual steps taken on both sides of the process (by the order filler and by the sales associate) can lead to inaccuracies and delay in both binning and picking up the merchandise.

This manual approach may result in some inefficiencies, inaccuracy, and employee and customer dissatisfaction. For example, disadvantages may include: delay resulting from order fillers placing the merchandise items in containers and recording the container location; delay resulting from the sales associate identifying and locating the correct container and then physically locating the merchandise item within the container; repeated back-and-forth travel by the employees; and possible increased wait time for customers.

Accordingly, there is a need for systems and methods that can improve the delivery of merchandise items between employees or areas in a shopping facility.

BRIEF DESCRIPTION OF THE DRAWINGS

Disclosed herein are embodiments of systems, apparatuses and methods pertaining systems and methods for delivering merchandise items using a conveyor apparatus. This description includes drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful to systems and methods for delivering merchandise items between various areas of a shopping facility. In one form, a system disclosed herein for delivering a merchandise item comprises: a conveyor apparatus having a plurality of unique conveyor locations for deposit of a merchandise item, the conveyor apparatus extending, at least in part, between a first controlled access point and a second, different controlled access point; a first input interface configured to enter identifying information regarding the merchandise item and to associate it with a corresponding unique conveyor location in the conveyor apparatus where the merchandise item is deposited; a second input interface configured to enter customer identification information; a controller configured to receive information from the first input interface and the second input interface and to activate the conveyor apparatus to move the corresponding unique location of the merchandise item to the second controlled access point; wherein the first controlled access point is accessible for depositing the merchandise item in a unique conveyor location and the second controlled access point is accessible for removing the merchandise item from the unique conveyor location.

In some forms, the conveyor apparatus may include a carousel track extending in a circuitous route through a secure area between the first and second controlled access points; and a plurality of containers for receiving merchandise items and for removably mounting to the unique conveyor locations along the carousel track. The carousel track may include a support mount at conveyor location along the carousel track for hanging each container. The controller may be configured to compare the information from the first input interface and the second input interface and to activate the conveyor apparatus when the identifying information regarding the merchandise item corresponds to the customer information. In addition, the conveyor apparatus may include a locking mechanism at each unique conveyor location for locking the merchandise item to the conveyor apparatus. The system may also include an actuator proximate the second controlled access point for release of the merchandise item from the conveyor apparatus.

The conveyor apparatus may also extend from the first and second controlled access points to a third different controlled access point, the third controlled access point being accessible for removal of the merchandise item from a conveyor location. Also, the system may include a controlled access point to identify the merchandise item for removal from the conveyor apparatus based on a predetermined condition of the merchandise item.

In another form, disclosed herein is a method for delivering a merchandise item comprising: depositing a merchandise item in a unique location in a conveyor apparatus at a first controlled access point; inputting first information identifying the merchandise item and its associated, corresponding unique location in the conveyor apparatus into a database; receiving second information identifying a customer and determining if the database contains corresponding identification information of the merchandise item; and if there is a match, activating, by a controller, the conveyor apparatus to move the associated unique conveyor location corresponding to the merchandise identification information to a second, different controlled access point.

In another form, disclosed herein is a system for delivering a prescription from a pharmacy to a cashier comprising: a conveyor apparatus having a plurality of unique conveyor locations for deposit of a prescription, the conveyor apparatus extending, at least in part, between a pharmacy access point and a cashier access point; a first input interface proximate the pharmacy access point configured to enter identifying information regarding the prescription and to associate it with a corresponding unique location in the conveyor apparatus where the prescription is deposited; a second input interface proximate the cashier access point configured to enter customer identification information; a controller configured to receive information from the first input interface and the second input interface and to activate the conveyor apparatus to move the corresponding unique conveyor location of the prescription to the cashier access point; wherein the conveyor apparatus is accessible at the pharmacy access point for depositing the prescription in a unique conveyor location and the conveyor apparatus is accessible at the cashier access point for removing the prescription from the unique conveyor location.

Figure 1:
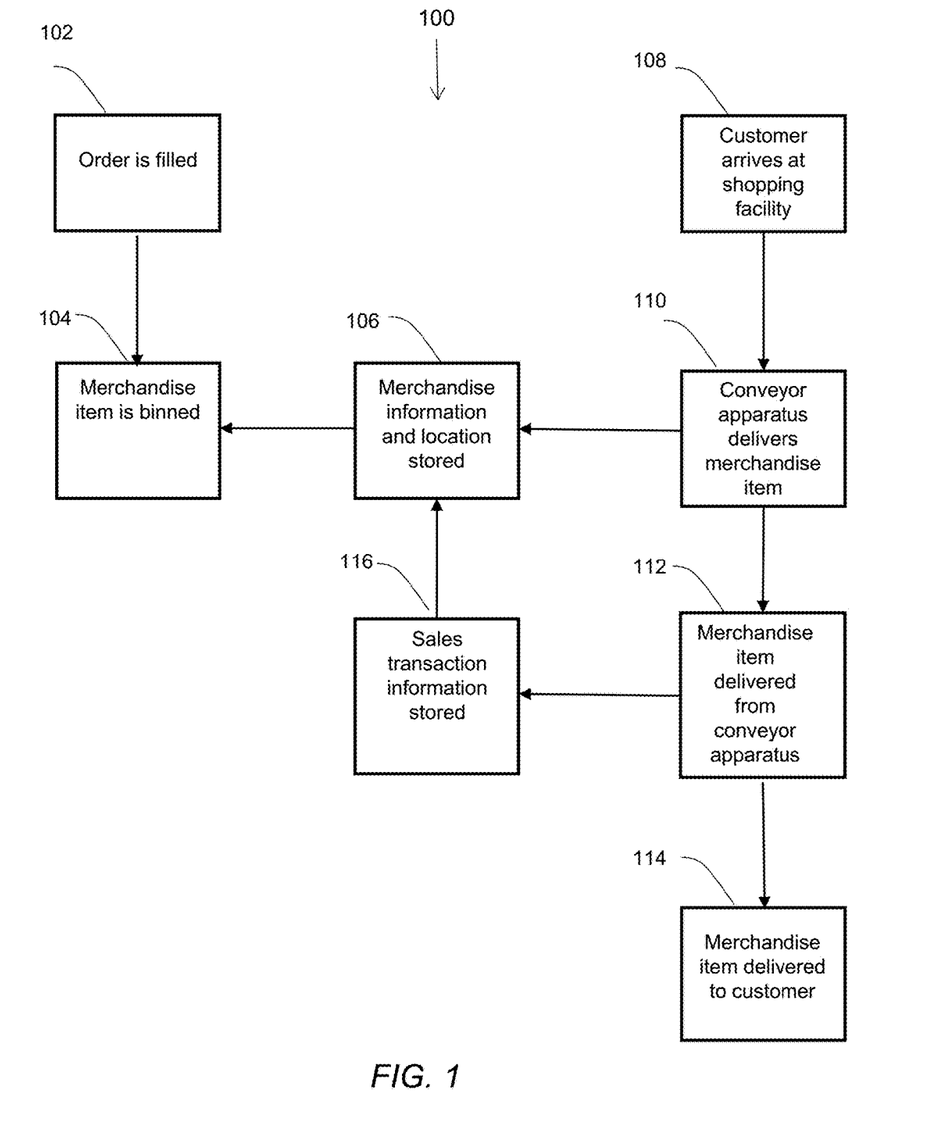
FIG. 1 is a flow diagram in accordance with some embodiments.

Referring to FIG. 1, there is shown a flow diagram for a process of delivering merchandise items using a conveyor apparatus to various controlled access points within a shopping facility. As can be seen in the diagram, the process includes two separate inputs (shown on the left hand and right hand parts of the diagram). Generally, as described below, the left hand side of the diagram shows the action by the merchandise order filler, and the right hand side shows the action at the point of sale controlled access point (which is shown to be a cashier controlled access point but could also be a customer self-serve controlled access point).

At block 102, on the left hand side of the diagram, this process 100 provides a step in which an employee fills an order for merchandise for a customer. Generally, it is contemplated that this process may be used for numerous types of merchandise. For example, it may be used in conjunction with the delivery of jewelry, electronics, mobile devices, and other high value merchandise. In one form, as addressed further below, the conveyor apparatus may provide a secure mechanism for delivery by traveling through a secure area with a limited number of controlled access points. Of course, it may also be used in conjunction with lower value merchandise, such as apparel, where security may be less significant.

At block 104, the order filler deposits a merchandise item on the conveyor apparatus and enters identification information in a database, i.e., it is binned. The merchandise item is preferably placed in some sort of container (bagged) and placed in a unique location on the conveyor apparatus, preferably the next available open location. The merchandise item and location information are entered into a database via a first input interface. The merchandise item and the location are preferably scanned so that the merchandise item and location are associated with one another and stored in a database. Although scanning a barcode is one option for entering this information in a database, it should be evident that many other input methods are available, including entering the information by a keyboard or register or through the use of a sensor mounted at or near the merchandise item and/or by the unique conveyor location. Any appropriate input interface may be used. In one form, it is contemplated that the binning action by the order filler will result in the merchandise item being locked to the conveyor apparatus. Once the order filler completes this binning action, his actions with respect to the order are finished. In other words, the order filler need not travel over to some remote common employee location, manually deposit the merchandise item in a storage area, manually record the location, and thereby deliver the merchandise item.

At block 106, the merchandise information and the corresponding unique conveyor location has been systematically stored in a database. This information generally includes identification information regarding the merchandise and customer and information regarding the conveyor location. Subsequently, as addressed below, when a customer arrives for pick-up, this information may be used to identify the merchandise location and automatically deliver it to the point of sale controlled access point.

At block 108, on the right hand side of the diagram, this process 100 provides a step in which a customer picks up the merchandise item. In this form, at block 108, the customer arrives and checks in with a cashier or sales associate. Although block 108 and the diagram addresses the involvement of a cashier, it should be evident that this process may involve a self-service customer point of sale controlled access point.

At block 110, the cashier enters customer identification information in a second input interface. In one form, the cashier may be prompted to select or pick one of various icons or prompts indicating the corresponding merchandise item. The second input interface communicates with the database to identify the corresponding unique conveyor location of the merchandise item. It is contemplated that any of various input interfaces may be used to enter the customer identification information. A controller then energizes the conveyor apparatus to cause it to move and deliver the merchandise item to the cashier's area.

At block 112, the cashier acts to systematically remove the merchandise item from the unique conveyor location. In one form, it is contemplated that the merchandise item has been locked to the conveyor apparatus and the cashier must take action to unlock the merchandise item. The cashier may activate this unlocking by any of various mechanisms, including by use of a release key on the input interface or by a separate release actuator located at the unique conveyor location. At block 114, the cashier then delivers the merchandise item to the customer. As stated above, this process 100 also contemplates delivery of the merchandise item directly to a customer via a customer self-service controlled access point.

At block 116, information regarding completion of the sales transaction may be systematically stored in the database. This information may include information about the customer, merchandise item, and unique conveyor location. For example, it may include a log of the sales activities. In addition, it may include updating the database to indicate that the merchandise item has been delivered and removed and that the unique conveyor location is available for deposit of a new merchandise item.

Figure 2:
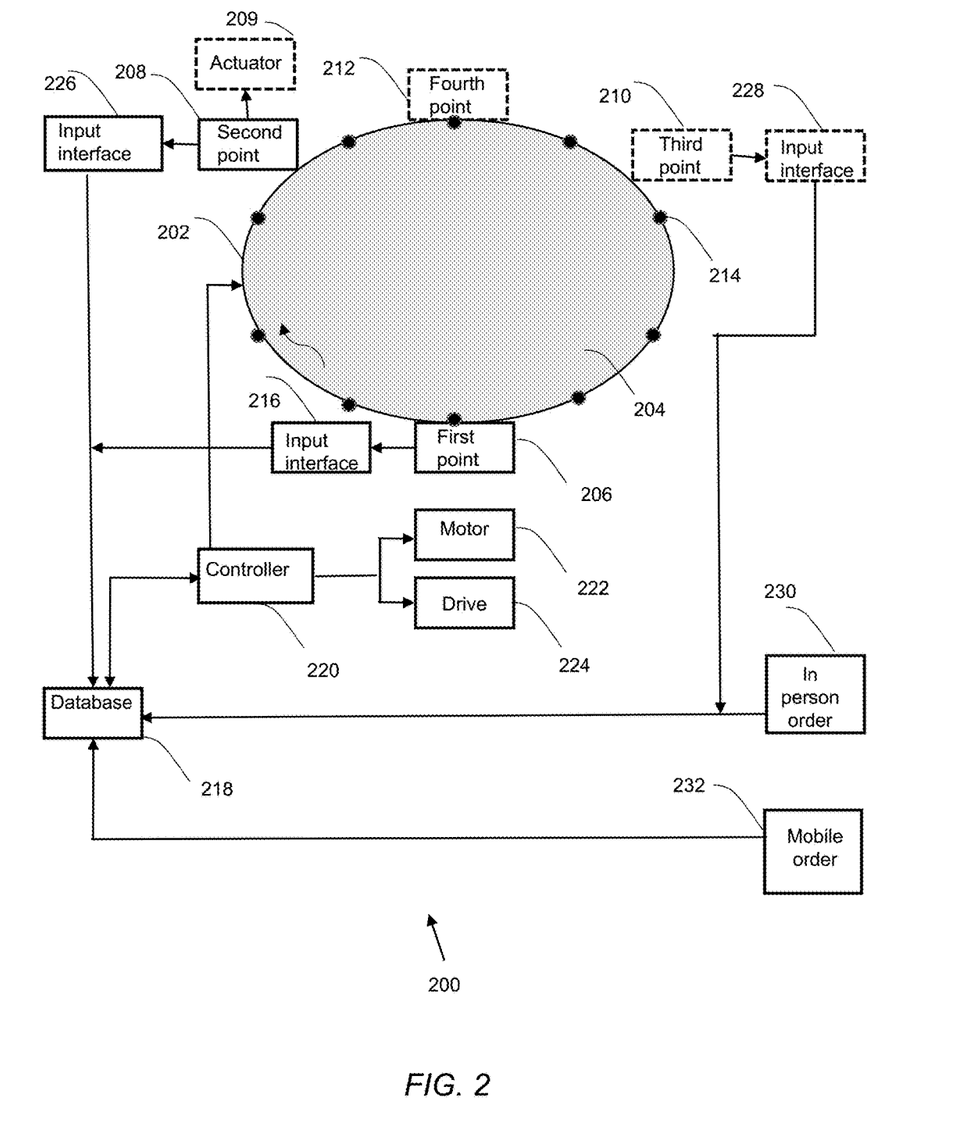
FIG. 2 is a block diagram in accordance with several embodiments.

Referring to FIG. 2, there is shown a system diagram showing various components for delivering merchandise items using a conveyor apparatus 202 to various controlled access points within a shopping facility. The order may be placed initially in any of various ways. For example, in one form, an order may be placed by a customer in person 230, or it may be placed remotely, such as via a mobile device 232. The information may then be entered into a database 218 that is accessible to an order filler. Alternatively, the information may be communicated directly to the order filler without entry in the database 218.

As can be seen in the diagram, the system 200 includes a conveyor apparatus 202 operating between multiple controlled access points. In one form, the system may include a conveyor apparatus 202 that moves through a secure area 204 and includes only two controlled access points, i.e., an order filler controlled access point 206 and a point of sale controlled access point 208. In another form, as described below, the system may include additional controlled access points. For example, the system may include controlled access points for an order filler 206, a cashier 208, a self-serve customer 210, and/or a maintenance employee 212.

FIG. 2 shows a conveyor apparatus 202 in the form of a carousel, or closed circuit loop, with multiple controlled access points. In one form, as addressed in more detail below, the conveyor apparatus 202 may be in the form of a carousel track/rail system that includes multiple interchangeable hanging containers that may each be mounted at a unique conveyor location 214. In one form, the hanging containers may each have sensors that can be linked and associated with sensors located at each of the unique conveyor locations 214. The track/rail system is operable such that each unique conveyor location 214 may be moved to a desired controlled access point along the circuitous route. In one form, the conveyor apparatus 202 preferably moves through a secure area 204 with limited access. The secure area 204 may be an area for holding inventory and may have a security fixture or other security apparatus limiting entry.

A first controlled access point is the order filler controlled access point 206. Information regarding the order may be available from a database 218 that is accessible to an order filler. As described above, the order filler bins or dispenses the merchandise item at this controlled access point by depositing the merchandise item on the conveyor apparatus 202 and entering merchandise and location identification information via an input interface 216 into the database 218. As can be seen in FIG. 2, the input interface 216 is in communication with database 218. The database 218 stores the merchandise information and its unique conveyor location 214 on the conveyor apparatus 202. The controller 220 is in communication with a motor 222 and drive 224 that are, in turn, coupled to the conveyor apparatus 202. The controller 220 may also be operable to lock the merchandise item to the unique conveyor location 214 when the merchandise item is deposited at this location. The controller 220 is configured to cause the conveyor apparatus 202 to move via motor 222 and drive 224 to deliver a unique conveyor location 214 to a desired controlled access point.

As described herein, the controller 220, or control circuit, can comprise a fixed-purpose hard-wired platform or can comprise a partially or wholly programmable platform, such as a microcontroller, an application specification integrated circuit, a field programmable gate array, and so on. These architectural options are well known and understood in the art and require no further description here. This control circuit 220 is configured (for example, by using corresponding programming stored in a memory as will be well understood by those skilled in the art) to carry out one or more of the steps, actions, and/or functions described herein.

Additionally, as described herein, the database 218 may be integrated into controller 220 or separate from it. The database 218 may be at the location of the shopping facility or remote from the shopping facility. Regardless of location, the database 218 comprises memory to store and organize certain data for use by the controller 220. In some forms, the database 218 may store data pertaining to one or more of: customer data, customer shopping data and patterns, merchandise and inventory data, unique conveyor location data, and so on.

In this illustrative example, the database 218 and controller 220 may be in wired or wireless communication with a plurality of input interface units. These teachings will accommodate a variety of input interface units including, but not limited to, mobile and/or handheld electronic devices such as so-called smart phones and portable computers such as tablet/pad-styled computers. Generally speaking, in one form, these input interface units should be able to wirelessly communicate via a wireless network, such as the wireless network of the shopping facility (such as a Wi-Fi wireless network). These input interface units generally provide a user interface for interaction with the system.

A second controlled access point is the cashier point of sale access point 208. As described above, the cashier enters customer identification information in an input interface 226. The input interface 226 is in communication with the database 218. The controller 220 is configured to compare the customer identification information from the cashier with the merchandise information from the order filler and determined if there is a match. If the controller 220 determines that there is a match, the controller 220 energizes the motor 222 and drive 224 to cause the unique conveyor location 214 corresponding to the merchandise item to be moved to the cashier controlled access point 208. The controller 220 may also be operable to unlock the merchandise item from the unique conveyor location 214 after the merchandise item arrives at the cashier controlled access point 208 and to activate a visual indicator at the unique conveyor location 214. Further, a push button or other type of actuator 209 may be located at or near the second controlled access point 208 or on the conveyor apparatus 202 for release of the merchandise item from the conveyor apparatus 202.

An optional third controlled access point is a customer self-serve access point 210 for controlled retrieval of the merchandise item by a customer. This customer controlled access point 210 may be used in lieu of or in addition to the cashier point of sale access point 208. At this point, the customer enters customer identification information in an input interface 228. Then, as with the cashier controlled access point 208, the controller 220 compares the customer identification information with the merchandise information, determines if there is a match, energizes the motor 222 and drive 224 (if there is a match), to move the unique conveyor location 214 to the self-serve customer controlled access point 210. The controller 220 may also be operable to unlock the merchandise item after the customer enters payment (or otherwise completes the transaction) and may also activate a visual indicator at the unique conveyor location 214.

An optional fourth controlled access point is a maintenance controlled access point 212. This fourth controlled access point 212 may be used by maintenance employees for repairing, cleaning, and otherwise maintaining the conveyor apparatus 202 and secure area 204. Alternatively, or in addition, this maintenance controlled access point 212 may be used for removal of merchandise items from the conveyor apparatus 202 based on a predetermined condition of the merchandise item. For example, the database 218 and controller 220 may be configured to identify merchandise items that should be released from the conveyor apparatus 202 because the merchandise item is expired, obsolete, or should be returned to stock merchandise (such as because the customer did not come to the shopping facility to pick up the merchandise item). The controller 220 may be further configured to bring those merchandise items to a central location point for removal from the conveyor apparatus 202.

Figure 3:
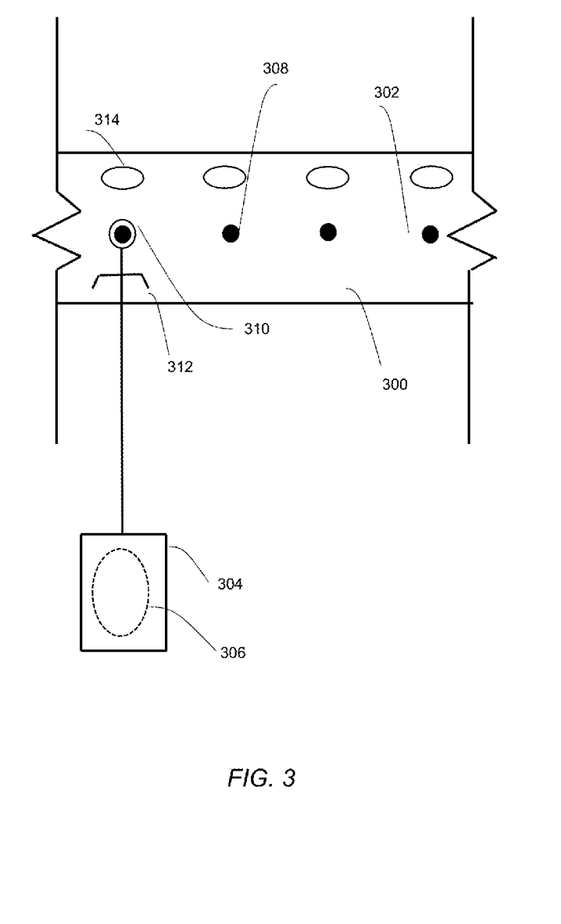
FIG. 3 is an illustration of a portion of a conveyor apparatus in accordance with several embodiments.

Referring to FIG. 3, there is shown a portion of an exemplary conveyor apparatus 300. As explained above, the conveyor apparatus 300 can be in the form of a carousel track that defines a closed circuit loop. As can be seen in FIG. 3, the conveyor apparatus 300 includes a number of unique conveyor locations 302 for mounting containers 304 holding merchandise item 306. In one form, as an order is filled, the order filler will place the merchandise item 306 in a new, interchangeable container 304 and will hang the container 304 on the next available open conveyor location 302. In one form, each conveyor location 302 may include a support mount 308 and each container 304 may have an opening 310 such that the container 304 can hang from the support mount 308. Further, each unique conveyor location 302 may be equipped with a locking mechanism assembly 312 such that the container 304 is secured to the conveyor apparatus 302. The controller locks the locking mechanism 312 when the container 304 is mounted to the conveyor apparatus 300 and unlocks the mechanism 312 when the container 304 has been transported to the intended controlled access point. In addition, each unique conveyor location 302 may include a visual indicator 314 that is activated when that location 302 has the desired merchandise item 306 in order to assist the employee or customer in identifying the location 302. Although one example of a conveyor apparatus 300 is shown, it should be evident that many other types and structures are possible for the conveyor apparatus.

Figure 4:
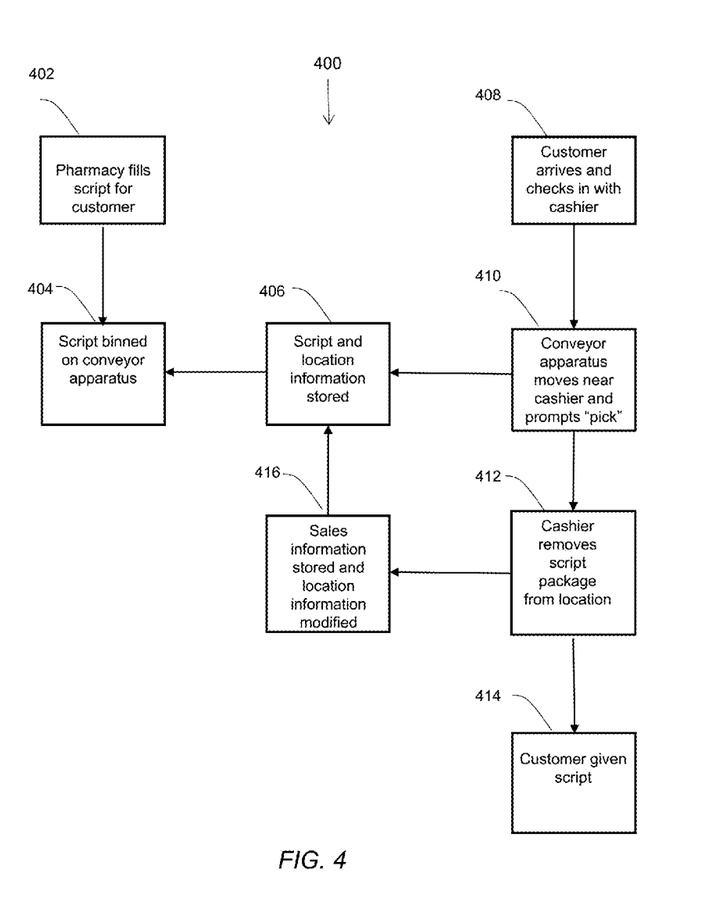
FIG. 4 is a flow diagram in accordance with some embodiments.

Referring to FIG. 4, there is shown a flow diagram showing a specific application of the process 400 to a shopping facility having a pharmacy. At block 402, a pharmacist or a pharmacist's assistant fills a prescription for a customer. At block 404, the pharmacist or assistant bins the script or prescription. In other words, the pharmacist or assistant may bag the script in a container, scan the script and its location on a carousel, and hang a container holding the script on the carousel. At block 406, the script and its location on the carousel have been associated with one another and stored in a database. The pharmacist/assistant's actions in the process are completed.

At block 408, the customer arrives and checks in with the cashier to pick up the script. At block 410, the cashier enters customer identification information in an input interface, which communicates with the database to identify the corresponding unique conveyor location of the script. A controller then energizes the conveyor apparatus to deliver the script to the cashier. At block 412, the cashier removes the script from the unique conveyor location. At block 414, the cashier then delivers the script to the customer. At block 416, information regarding the sales transaction may be stored in the database, including updating the database to indicate that the script was picked up and that the unique conveyor location is available for hanging a new script.

Although the process 400 shows delivery to a cashier, it should be evident that the cashier may be replaced by a self-service customer. In other words, the cashier controlled access point may be replaced by a self-serve customer controlled access point. The process 400 is generally similar, but where a self-serve customer controlled access point is used, it is preferable to also include an unlocking step to unlock the script from the carousel when the customer completes the sales transaction.

Figure 5:
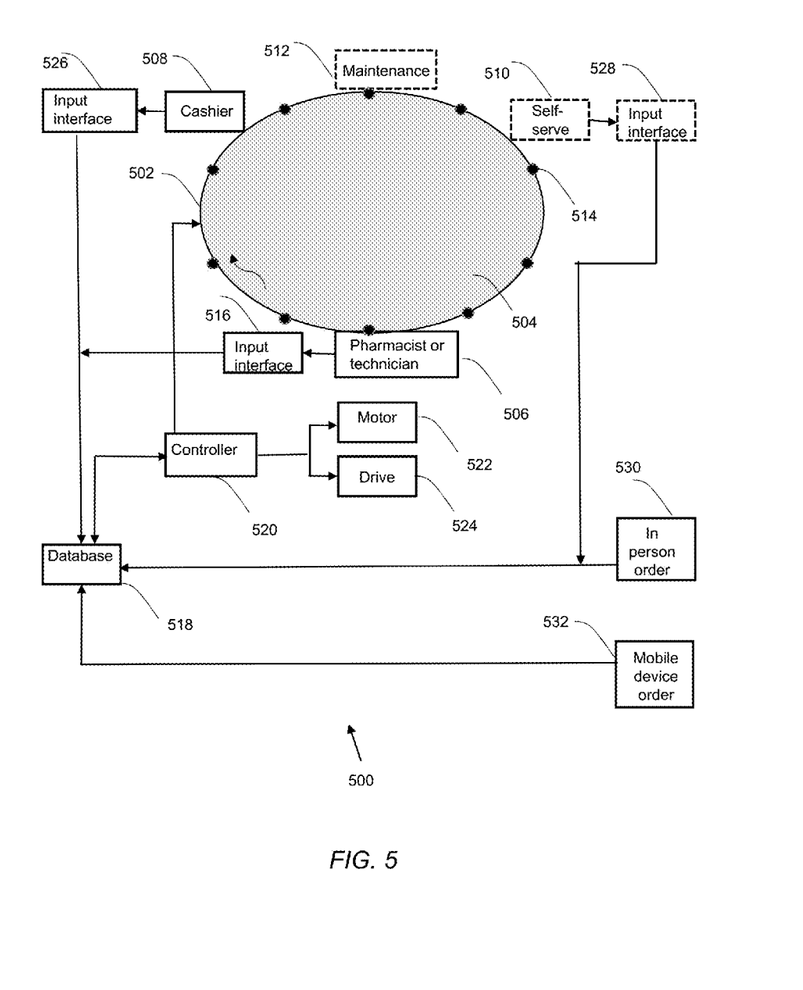
FIG. 5 is a block diagram in accordance with several embodiments.

FIG. 5 is a system diagram showing another specific application to a shopping facility having a pharmacy. Initially, order information may be stored in a database 518 in any of various ways, including in person orders 530 or by mobile device orders 532. As shown in FIG. 5, the system 500 includes a conveyor apparatus 502 in the form of a carousel operating in a secure area 504 with two controlled access points. A pharmacy technician has access to a controlled access point 506 in the pharmacy, and a cashier has access to a controlled access point 508 in a cashier area. As can be seen, when the order is placed, the pharmacy technician gathers the prescription from the inventory and then bins it in a unique conveyor location 514 at the controlled access point 506. This information is transmitted to a database 518 via an input interface 516. When the customer later comes in to pick up the order, the cashier enters the customer's information at an input interface 526, which, in turn, causes a controller 520 to activate a motor 522 and drive 524 to cause the carousel to deliver the prescription in the unique conveyor location to the controlled access point 508 in the cashier area.

FIG. 5 also shows an optional controlled access point 510 in a customer self-service area. When the customer enters identification information at this controlled access point 510 via input interface 528, the customer activates the carousel to deliver the prescription in the unique conveyor location 514 to the self-service area. The system 500 may also optionally include a maintenance controlled access point 512 for maintenance of the secure area 504 or for removing a merchandise item based on the condition of the item, including a customer's failure to pick up the prescription.

As described earlier, the system 500 creates an easy to locate queue for scripts, in lieu of a manual approach of depositing scripts in bins that a cashier must then travel to and search through to locate the correct script. In this form, the conveyor apparatus may be a carousel placed between the pharmacist and cashier. In one form, when the pharmacist or technician is done filling the script, he places it into a hangable container, scans an identifying label (either on the script or on the container) and hangs the container onto an empty slot of the carousel. The system 500 can assign a location to the slot that the pharmacist or technician can scan or key in, or a sensor may detect the assigned location. The container is systematically assigned to a location staged for customer pick-up. When the customer arrives, the cashier looks up the customer's identification information and activates the carousel to bring the location of the script near the cashier. A light flashing near the package or other visual indicator may be used to assist the cashier in locating the correct container. After the cashier selects the container, the container can push a button or other actuator on the light or near the light to systematically remove the container and its contents from the location.

Figure 6:
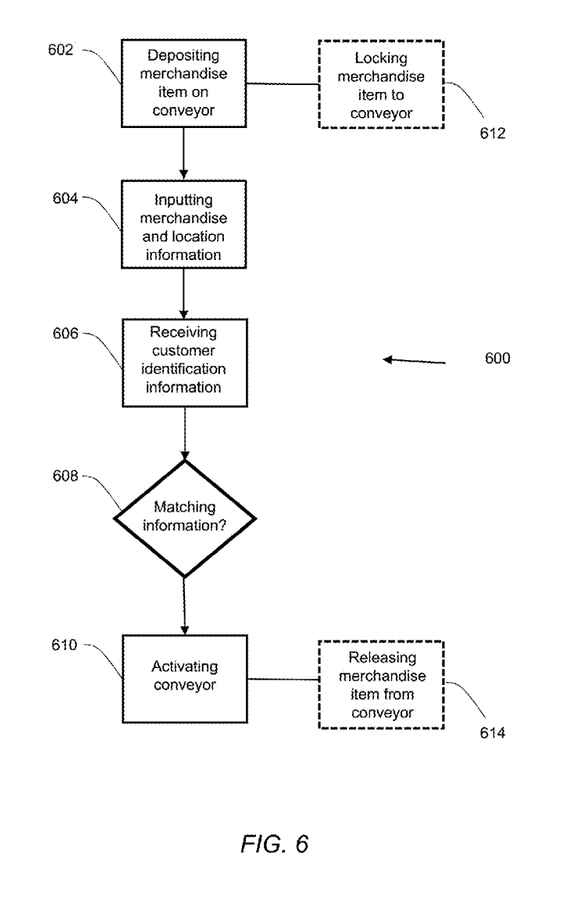
FIG. 6 is a simplified flow diagram in accordance with some embodiments.

Referring to FIG. 6, there is shown a simplified flow diagram of a general process 600. At block 602, a merchandise item is deposited in a unique location in a conveyor apparatus at a first controlled access point. At block 604, information identifying the merchandise item and its associated, corresponding unique location in the conveyor apparatus is inputted into a database. At block 606, information identifying a customer is received. At block 608, it is determined if the database contains corresponding identification information of the merchandise item. If there is a match, at block 610, the conveyor apparatus is activated to move the associated unique conveyor location corresponding to the merchandise identification information to a second, different controlled access point. As shown in blocks 612 and 614, the merchandise item may also be locked to the conveyor apparatus after deposit and may be released from the conveyor apparatus after movement of the conveyor apparatus.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for delivering a merchandise item between an order filling station and a cashier station at a shopping facility, the system comprising:
   an order filling station and a cashier station located in separate physical areas of a shopping facility;
   a first controlled access point at the order filling station;
   a second controlled access point at the cashier station;
   a conveyor apparatus extending along a carousel track defining a circuitous route between the first controlled access point at the order filling station and the second controlled access point at the cashier station and having a plurality of uniquely identified conveyor locations for deposit of a merchandise item, the conveyor apparatus extending, at least in part, between the first controlled access point and the second controlled access point;
   a first input interface at the order filling station configured to enter identifying information regarding the merchandise item and to associate the merchandise item with a corresponding uniquely identified conveyor location in the conveyor apparatus where the merchandise item is deposited;
   a second input interface at the cashier station configured to enter customer identification information;
   a controller configured to receive information from the first input interface and the second input interface and to activate the conveyor apparatus to move the corresponding uniquely identified location of the merchandise item to the second controlled access point;
   wherein the first controlled access point is accessible for depositing the merchandise item in a uniquely identified conveyor location and the second controlled access point is accessible for removing the merchandise item from the uniquely identified conveyor location.

2. The system of claim 1, wherein the conveyor apparatus comprises:
   a plurality of containers for receiving merchandise items and for removably mounting to the uniquely identified conveyor locations along the carousel track.

3. The system of claim 2, wherein the carousel track includes a support mount at each uniquely identified conveyor location along the carousel track for hanging each container.

4. The system of claim 1, wherein the first and second input interfaces comprise one or more of a barcode scanner, a keyboard interface, and a sensor disposed at a uniquely identified conveyor location.

5. The system of claim 1, wherein the controller is configured to compare the information from the first input interface and the second input interface and to activate the conveyor apparatus when the identifying information regarding the merchandise item corresponds to the customer information.

6. The system of claim 1, wherein the conveyor apparatus includes a locking mechanism at each uniquely identified conveyor location for locking the merchandise item to the conveyor apparatus.

7. The system of claim 6, further comprising an actuator proximate the second controlled access point for release of the merchandise item from the conveyor apparatus.

8. The system of claim 1, wherein:
   the conveyor apparatus includes a visual indicator at each uniquely identified conveyor location; and
   the controller is configured to activate the visual indicator corresponding to the location of the merchandise item.

9. The system of claim 1, further comprising:
   a self-serve customer pick-up station at a location physically separate from the order filling station and the cashier station; and
   a third controlled access point at the self-serve customer pick-up station;
   wherein the circuitous route of the conveyor apparatus extends from the first and second controlled access points to the third controlled access point at the self-serve customer pick-up station, the third controlled access point being accessible for removal of the merchandise item from a uniquely identified conveyor location.

10. The system of claim 1, further comprising:
    a station for maintenance of the conveyor apparatus, the maintenance station being physically separate from the order filling station and the cashier station; and
    a fourth controlled access point at the maintenance station;
    wherein the circuitous route of the conveyor apparatus extends from the first and second controlled access points to the fourth controlled access point at the maintenance station, the fourth controlled access point being accessible for maintenance of the conveyor apparatus.

11. A method for delivering a merchandise item between an order filling station and a cashier station at a shopping facility, the method comprising:

provliding an order filling station and a cashier station located in separate physical areas of a shopping facility;

providing a first controlled access point at the order filling station;

providing a second controlled access point at the cashier station;

providing a conveyor apparatus extending along a carousel track defining a circuitous route between the order filling station and the cashier station and having a plurality of uniquely identified conveyor locations for deposit of a merchandise item, the conveyor apparatus extending, at least in part, between the first controlled access point at the order filling station and the second controlled access point at the cashier station;

depositing a merchandise item in a uniquely identified location in a conveyor apparatus at the first controlled access point;

inputting first information identifying the merchandise item and its associated, corresponding uniquely identified location in the conveyor apparatus into a database;

receiving second information identifying a customer and determining if the database contains corresponding identification information of the merchandise item; and if there is a match, activating, by a controller, the conveyor apparatus to move the associated uniquely identified conveyor location corresponding to the merchandise identification information to the second controlled access point.

12. The method of claim 11, wherein the depositing of the merchandise item in a uniquely identified location in a conveyor apparatus comprises placing the merchandise item in one of a plurality of containers removably mounted to the carousel track extending between the first and second controlled access points.

13. The method of claim 11, wherein the inputting of information comprises one or more of scanning a barcode, using a keyboard, or inputting by sensor.

14. The method of claim 11, further comprising comparing the first and second information and activating the conveyor apparatus when the identifying information regarding the merchandise item corresponds to the customer information.

15. The method of claim 11, further comprising locking the merchandise item to the conveyor apparatus proximate the first controlled access point and releasing the merchandise item proximate the second controlled access point.

16. The method of claim 11, further comprising activating a visual indicator corresponding to the uniquely identified location of the merchandise item.

17. The method of claim 11, further comprising:

providing a self-serve customer pick-up station at a location physically separate from the order filling station and the cashier station; and providing a third controlled access point at the self-serve customer pick-up station;

wherein the carousel track extends from the first and second controlled access points to the third controlled access point at the self-serve customer pick-up station, the third controlled access point being accessible for removal of the merchandise item from the uniquely identified conveyor location.

18. The method of claim 11, wherein depositing a merchandise item in a uniquely identified location further comprises depositing the merchandise item in the next available uniquely identified conveyor location of a plurality of locations arranged in a queue along the conveyor apparatus.

19. The method of claim 11, further comprising identifying the merchandise item for removal from the conveyor apparatus based on a predetermined condition of the merchandise item.

20. A system for delivering a prescription from a pharmacy station to a cashier station at a shopping facility, the system comprising:

a pharmacy station and a cashier station located in separate physical areas of a shopping facility;

a first controlled access point at the pharmacy station;

a second controlled access point at the cashier station;

a conveyor apparatus extending along a carousel track defining a circuitous route through a secure area between the pharmacy station and the cashier station and having a plurality of uniquely identified conveyor locations for deposit of a prescription, the conveyor apparatus extending, at least in part, between the first controlled access point at the pharmacy station and the second controlled access point at the cashier station;

a first input interface proximate the first controlled access point configured to enter identifying information regarding the prescription and to associate it with a corresponding uniquely identified location in the conveyor apparatus where the prescription is deposited;

a second input interface proximate the second controlled access point configured to enter customer identification information;

a controller configured to receive information from the first input interface and the second input interface and to activate the conveyor apparatus to move the corresponding uniquely identified conveyor location of the prescription to the second controlled access point;

wherein the conveyor apparatus is accessible at the first controlled access point for depositing the prescription in a uniquely identified conveyor location and the conveyor apparatus is accessible at the second controlled access point for removing the prescription from the uniquely identified conveyor location.

21. The system of claim 20, wherein the conveyor apparatus comprises:

a plurality of removable containers for receiving merchandise items and for hanging at the uniquely identified conveyor locations along the carousel track.

22. The system of claim 20, further comprising:

a self-serve customer pick-up station at a location physically separate from the pharmacy station and the cashier station; and a third controlled access point at the self-serve customer pick-up station;

wherein the circuitous route of the conveyor apparatus extends from the first controlled access point to the second controlled access point to the third controlled access point for controlled retrieval by a customer.

\* \* \* \* \*